(12) United States Patent
Kanda et al.

(10) Patent No.: US 8,767,212 B2
(45) Date of Patent: Jul. 1, 2014

(54) DEVICES AND METHODS FOR DETECTING AND SORTING BIOLOGICAL PARTICLES IN A LIQUID FLOW USING SUBSTANTIALLY UNIFORM INTENSITY ALONG A DIRECTION OF FLOW OF A FLOW CELL

(75) Inventors: Masahiko Kanda, Hyogo (JP); Shigeaki Kato, Tokyo (JP); Sari Fujiyama, Tokyo (JP); Kei Izumikawa, Tokyo (JP); Toshihiro Chikanishi, Tokyo (JP)

(73) Assignee: Bay Bioscience Kabushiki Kaisha, Hyogo (JP)

( * ) Notice: Subject to any disclaimer, the term of this patent is extended or adjusted under 35 U.S.C. 154(b) by 359 days.

(21) Appl. No.: 12/923,687

(22) Filed: Oct. 4, 2010

(65) Prior Publication Data

US 2011/0176127 A1 Jul. 21, 2011

(30) Foreign Application Priority Data

Oct. 5, 2009 (JP) ................................ 2009-231468

(51) Int. Cl.
*G01N 21/00* (2006.01)
(52) U.S. Cl.
USPC .......................................... 356/442; 356/338
(58) Field of Classification Search
USPC .................. 356/411, 423–444, 335–339, 343
See application file for complete search history.

(56) References Cited

U.S. PATENT DOCUMENTS

| | | | | |
|---|---|---|---|---|
| 3,510,648 A * | 5/1970 | Alton, Jr. | ....................... | 250/364 |
| 4,327,972 A | 5/1982 | Brunsting | | |
| 5,274,227 A * | 12/1993 | Moring | .................... | 250/227.25 |
| 7,417,734 B2 | 8/2008 | Kanda | | |
| 7,443,491 B2 | 10/2008 | Kanda | | |
| 7,876,436 B2 | 1/2011 | Chu | | |
| 2005/0030519 A1 | 2/2005 | Roth | | |
| 2005/0072909 A1* | 4/2005 | Corson | ........................ | 250/226 |
| 2007/0195310 A1 | 8/2007 | Kanda | | |
| 2008/0151240 A1* | 6/2008 | Roth | ............................. | 356/317 |
| 2009/0122311 A1 | 5/2009 | Kanda | | |
| 2010/0297759 A1 | 11/2010 | Kanda | | |

FOREIGN PATENT DOCUMENTS

| | | | | |
|---|---|---|---|---|
| JP | 2005-315799 | | 11/2005 | |
| JP | 2007-501394 | | 1/2007 | |
| JP | 2008-089540 | | 4/2008 | |
| WO | WO2009078307 | * | 6/2009 | ............. G01N 15/14 |

OTHER PUBLICATIONS

Japanese Office Action and English translation thereof dated Dec. 24, 2013.

* cited by examiner

*Primary Examiner* — Tarifur Chowdhury
*Assistant Examiner* — Michael P Lapage
(74) *Attorney, Agent, or Firm* — Harness, Dickey & Pierce, P.L.C.

(57) ABSTRACT

In at least one embodiment, a flow cytometer includes a flow cell defining a sheath flow encompassing a dyed biological particle, a first optical source irradiating first light onto the flow cell, a second optical source irradiating second light onto the flow cell downstream where the first light is irradiated, a first optical detector detecting scattered light or fluorescence from the biological particle to output a first electrical signal corresponding thereto, a plurality of second optical detectors arranged along the flow cell, each of the second optical detectors detecting fluorescence from the biological particle to output a second electrical signal corresponding thereto, and a signal processor summing the second electrical signals output from the plurality of the second optical detectors in a plurality of time windows estimated based upon when the first optical detector detects the scattered light or the fluorescence, thereby to increase the second electrical signals of the fluorescence from the biological particle excited by the second light.

13 Claims, 15 Drawing Sheets

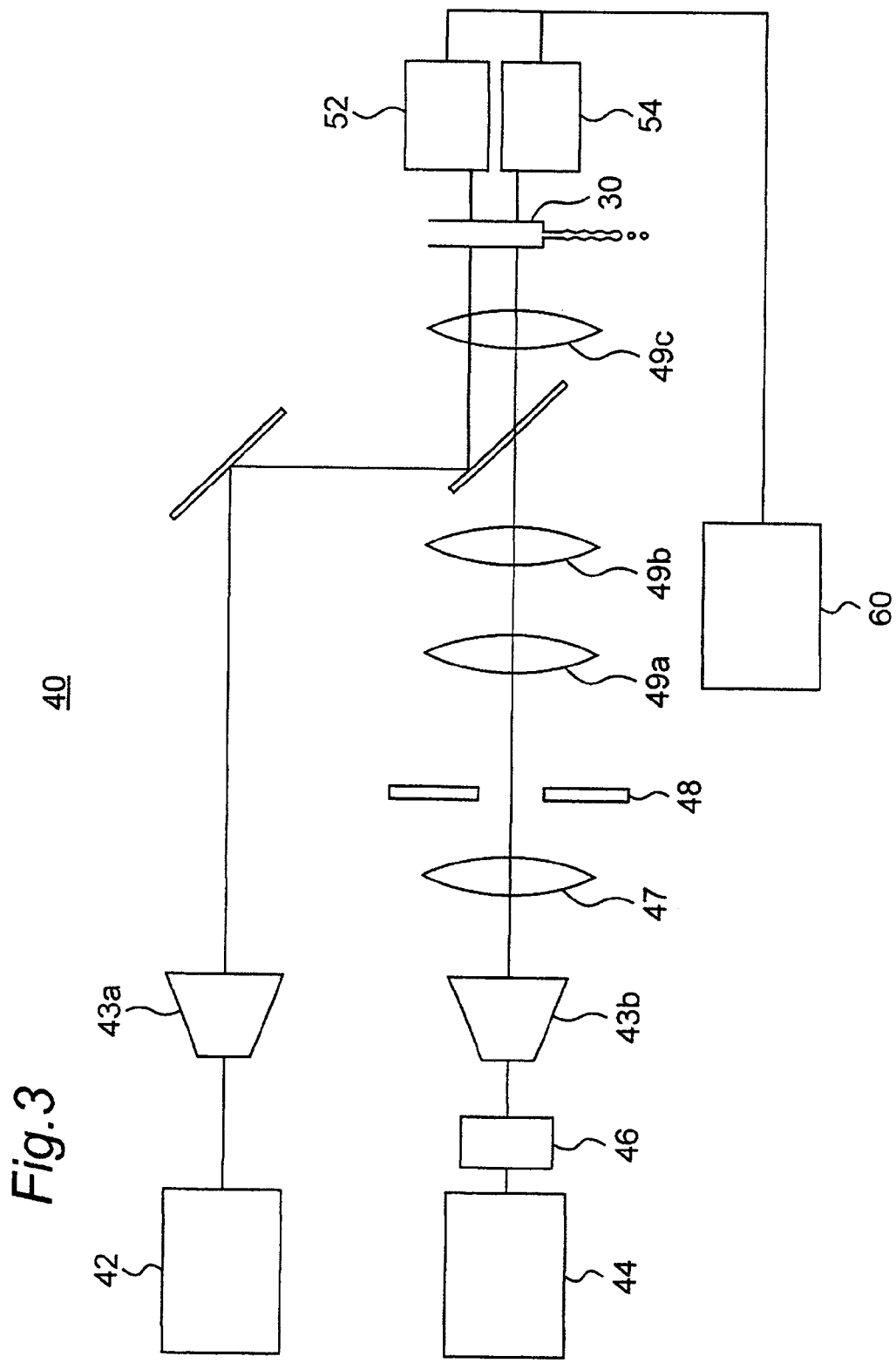

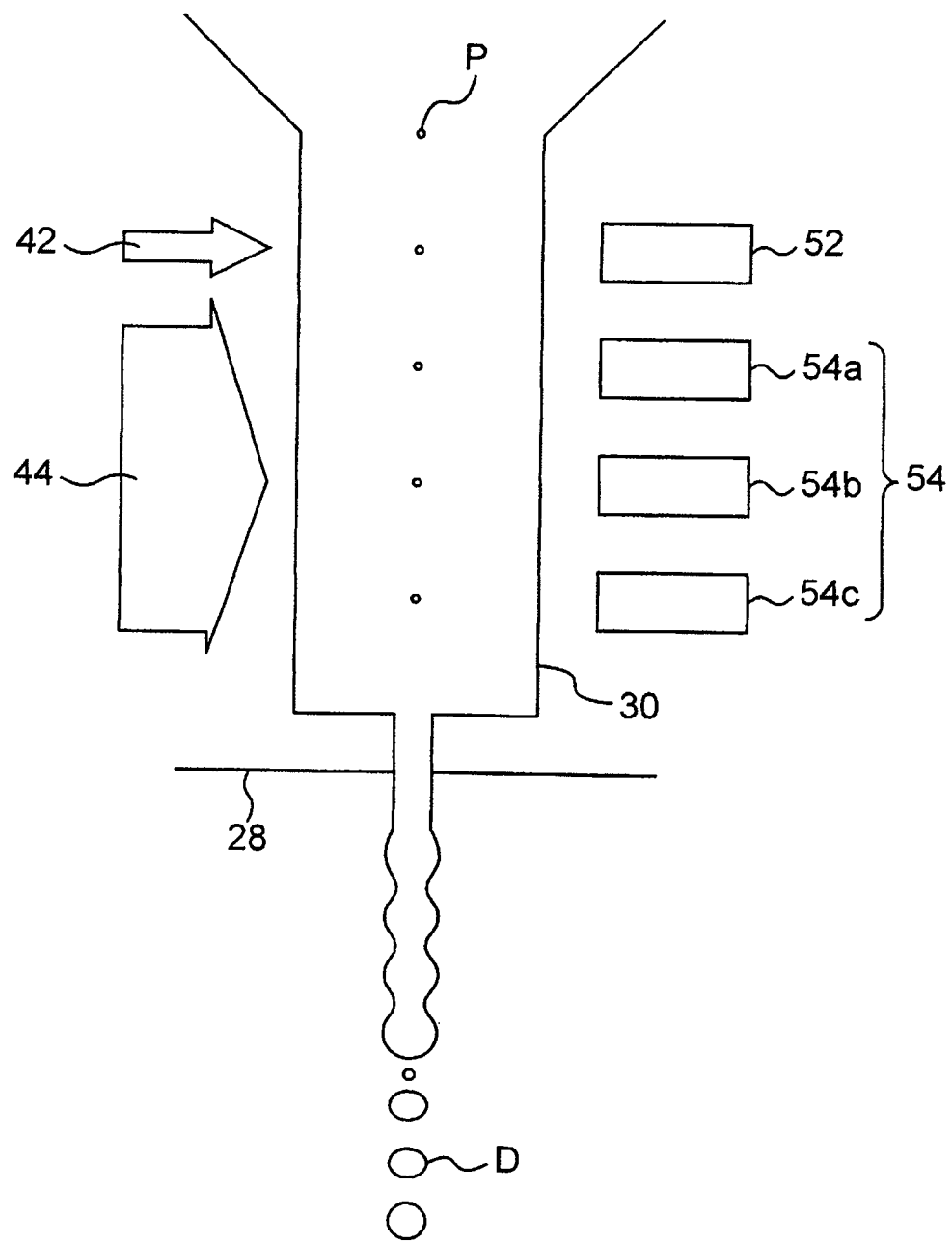

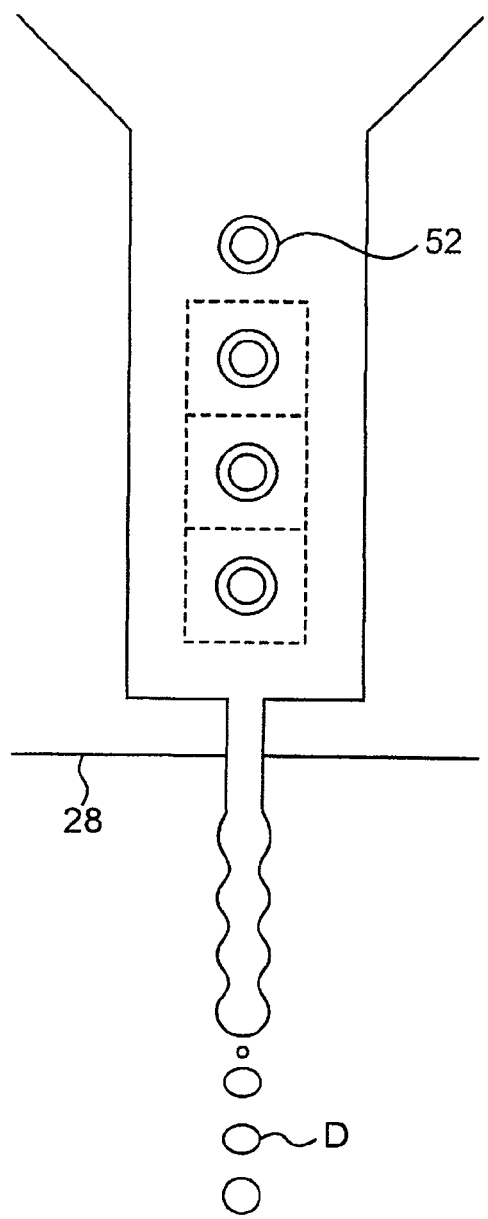 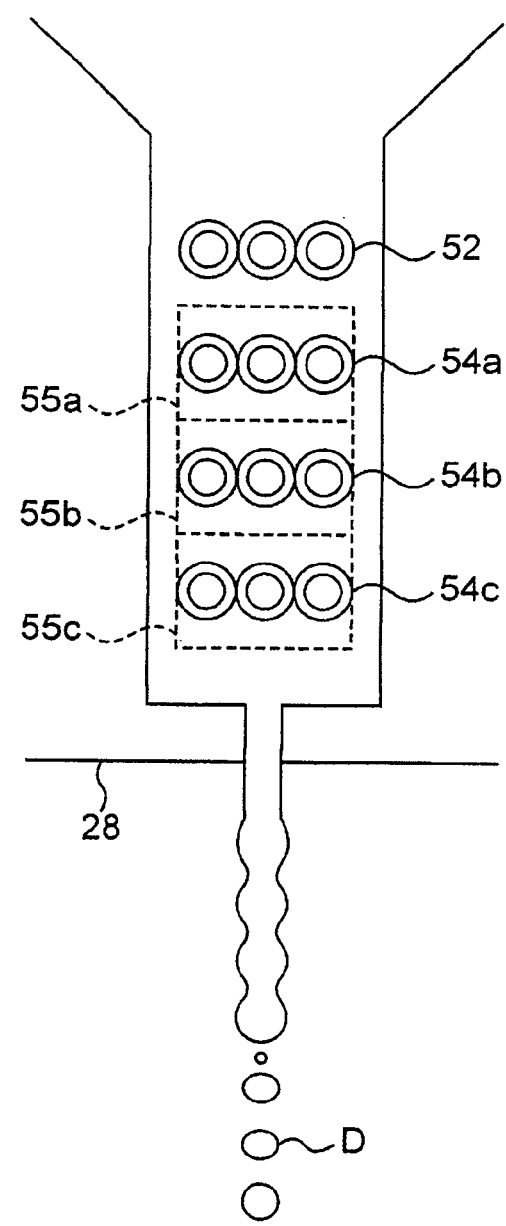

FIRST OPTICAL DETECTOR 52

SECOND OPTICAL DETECTOR 54a
(RECEIVING REGION 55a)

SECOND OPTICAL DETECTOR 54b
(RECEIVING REGION 55b)

SECOND OPTICAL DETECTOR 54c
(RECEIVING REGION 55c)

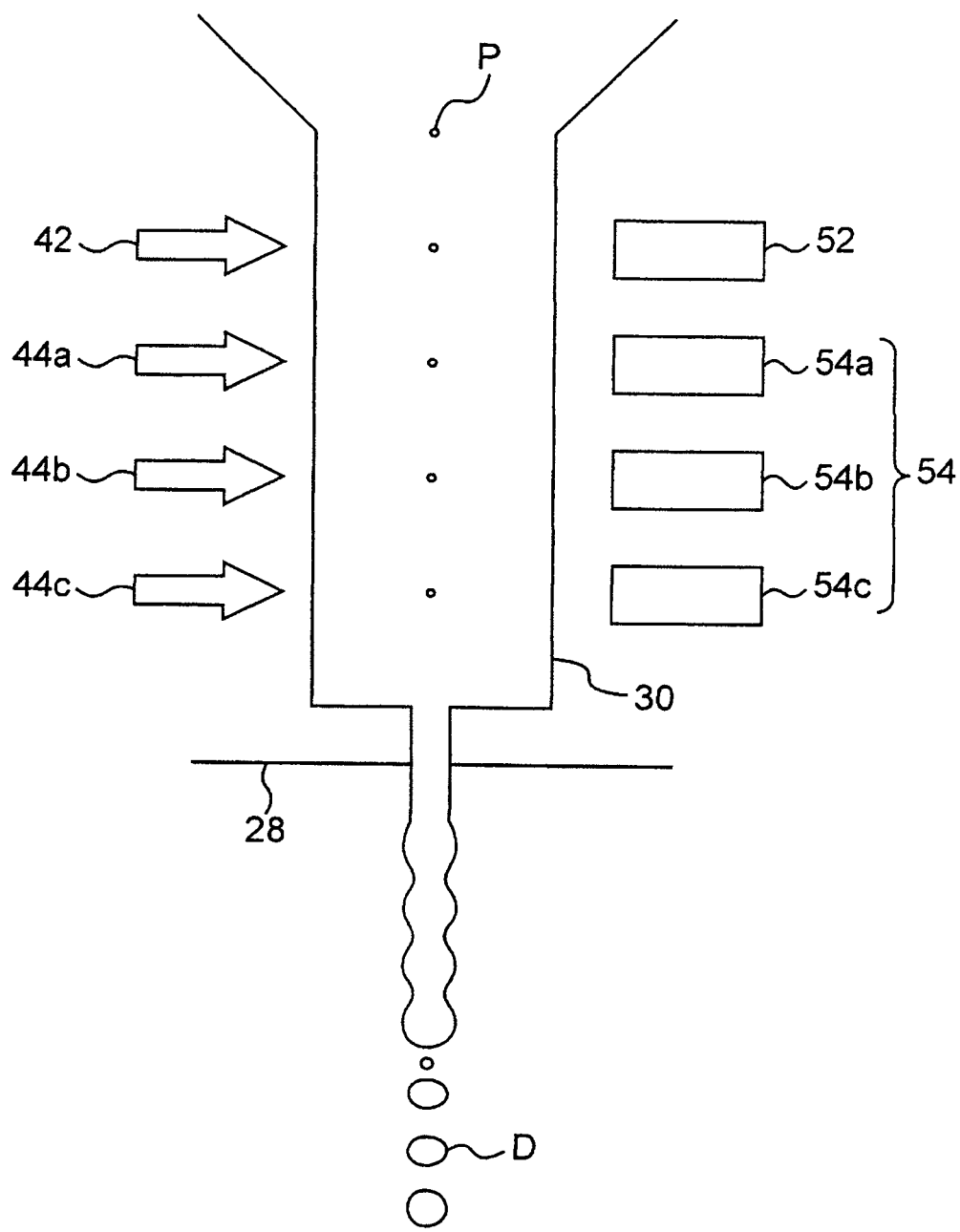

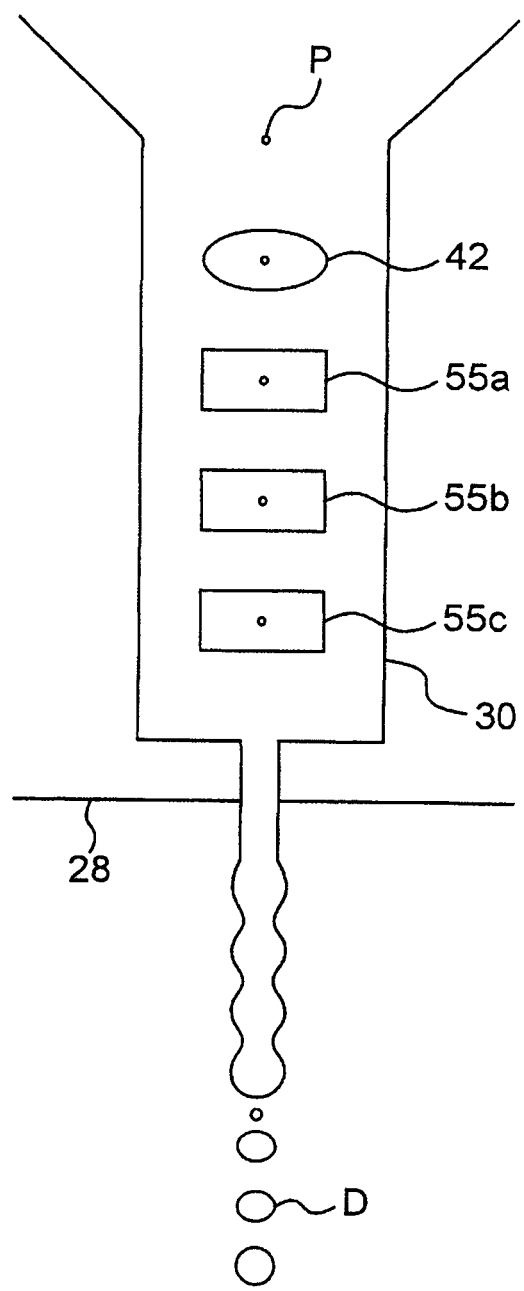

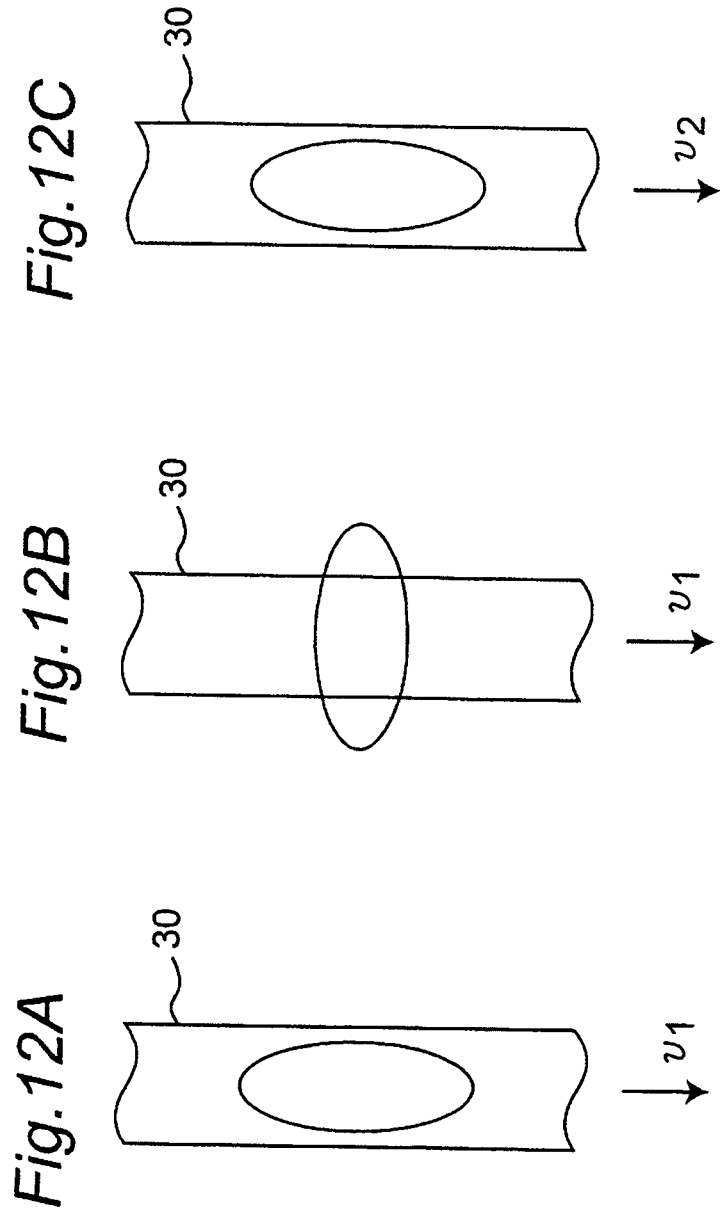

DEVICES AND METHODS FOR DETECTING AND SORTING BIOLOGICAL PARTICLES IN A LIQUID FLOW USING SUBSTANTIALLY UNIFORM INTENSITY ALONG A DIRECTION OF FLOW OF A FLOW CELL

TECHNICAL FIELD

The present invention relates to a flow cytometer and a flow cytometry.

BACKGROUND ART

Recent rapid development of the biotechnology expands a demand of a flow cytometer and a cell sorter which are more commonly used in the various fields of medicine and biology for automatic analysis and fractionation of multiple cells. In general, the flow cytometer forms a stream of a sheath flow containing various cell particles in line, which are collected from a living body (blood, etc.) and dyed with a fluorescent labeling reagent, and emits laser beam onto the stream of the cell particles to detect light excited by and/or scattered at the cell particles (i.e., forward-scattered light, and side-scattered light, and multicolor fluorescence varying based on the fluorescent labeling reagent used) so that each of the cell particles in the stream is analyzed based upon the detected light In general, the flow cytometer converts the detected light having identification information of the cell particles into electrical signals, so as to statistically evaluate electrical signals for a mass of the cells collected from the sample, thereby allowing diagnosis of a health condition such as a disease of the living body. Further, the cell sorter also uses the electrical signals having identification information to selectively charge droplets containing a particular group of the cells to be sorted, and applying a DC electric field across a dropping path of the droplets, thereby selectively retrieving or sorting the desired cells.

Typical flow cytometers have been suggested, for example by Patent Documents 1 and 2 commonly assigned to the present applicant, all of which disclosure are incorporated herein by reference.

Such conventional flow cytometers or cell sorters have a main or principal purpose in identifying or sorting relatively bulky cell particles collected from the blood. Meantime, as gene analysis research such as human genome decoding research has been more intensively progressed, more demand has been grown for a new technique to identify and sort not only the bulky cell particles but also fine protein complexes precisely by the fluorescent labeling approach.

PRIOR PATENT DOCUMENTS

Patent Document 1: JP 3891925, B (of which patent family is U.S. Pat. No. 7,443,491, B2)
Patent Document 2: JP 3891925, B (of which patent family is U.S. Pat. No. 7,417,734, B2)

DISCLOSURE OF INVENTION

Problems to be Solved by Invention

However, the conventional flow cytometers or cell sorters have a problem to be solved, for precisely identifying and sorting fine protein complexes by means of the fluorescent labeling technique. That is, a relatively large or bulky cell particle, of which diameter $D_1$ falls within 0.5 micrometers through several hundreds micrometers as shown in FIG. 11A, likely receives a lot of antibodies labeled with fluorescent dye on the surface of which area are proportional to the diameter. Contrary, a small or fine protein complex, of which diameter $D_2$ is less than several tens nanometers as shown in FIG. 11B, can catch few antibodies labeled with fluorescent dye. Thus, fluorescence intensity from the labeled protein complex is substantially faint comparing to that from the bulky cell particle. For instance, when the protein complex has diameter $D_2$ of one-tenth of diameter $D_1$ of the cell particle (i.e., $D_2/D_1=1/10$), fluorescence intensity from the labeled protein complex is one-hundredth (i.e., $1/100$) of that from the cell particle, in proportion to square of the diameter ratio. Therefore, the conventional flow cytometers or cell sorters receive such insufficient fluorescence intensity from the fine protein complexes that precise identification and sorting is hardly practical for the fine protein complexes.

Means to Solve the Problems

The present invention is made for solving such a problem, and one aspect of the present invention is to provide a flow cytometer as follows. That is, the flow cytometer comprises a flow cell defining a sheath flow encompassing a dyed biological particle, a first optical source irradiating first light onto the flow cell, a second optical source irradiating second light onto the flow cell downstream where the first light is irradiated, a first optical detector detecting scattered light or fluorescence from the biological particle to output a first electrical signal corresponding thereto, a plurality of second optical detectors arranged along the flow cell, each of the second optical detectors detecting fluorescence from the biological particle to output a second electrical signal corresponding thereto, and a signal processor summing the second electrical signals output from the plurality of the second optical detectors in a plurality of time windows estimated based upon when the first optical detector detects the scattered light or the fluorescence, thereby to increase the second electrical signals of the fluorescence from the biological particle excited by the second light.

Preferably, the second optical source irradiates the second light of substantially uniform intensity across a light receiving region of the flow cell opposing to the plurality of the second optical detectors. Also, the second optical source may include a plurality of optical sources, each of which irradiating the second light having the same wavelength across one of light receiving regions of the flow cell opposing to the respective one of the second optical detectors. Further, the second optical source may include an array of optical sources arranged in a first direction along the sheath flow and a second direction perpendicular to the first direction. More preferably, the flow cytometer further comprises a plurality of microscopic lens opposing to the second optical detectors, respectively, for focusing the fluorescence from the cell particle into the second optical detectors.

Another aspect of the present invention is to provide a flow cytometry, which comprises steps of defining a sheath flow encompassing a dyed biological particle, irradiating first light onto the flow cell, irradiating second light onto the flow cell downstream where the first light is irradiated, detecting scattered light or fluorescence from the biological particle to output a first electrical signal corresponding thereto, detecting fluorescence from the biological particle in a plurality of light receiving regions to output a second electrical signal corresponding thereto, and summing the second electrical signals output from the plurality of the second optical detectors in a plurality of time windows estimated based upon when the first optical detector detects the scattered light or the fluorescence, thereby to increase the second electrical signals of the fluorescence from the biological particle excited by the second light.

Similar in the flow cytometry, it is preferable that the second light is irradiated with substantially uniform intensity across a light receiving region of the flow cell opposing to the plurality of the second optical detectors. Alternatively, the second light may have the same wavelength and may be irradiated across one of light receiving regions of the flow cell opposing to the respective one of the second optical detectors.

Advantages of Invention

As above, by electrically summing the second electrical signals output from a plurality of the second optical detectors, it is possible to increase the second electrical signals of the fluorescence from the biological particle excited by the second light. Therefore, the detecting accuracy is substantially improved even for the fine biological particles such as fine protein complexes. Also, the second optical source irradiates the second light of substantially uniform intensity across a light receiving region of the flow cell opposing to the plurality of the second optical detectors so that the excitation time for the fine biological particles can be extended to increase the fluorescence intensity.

BRIEF DESCRIPTION OF DRAWINGS

FIG. 3 is a schematic view of the optical mechanism shown in FIG. 1, showing several components thereof.

FIG. 4 is a schematic cross sectional view of the flow cell of FIG. 2, showing the incident laser beams onto the flow cell, and schematic structure of the optical detectors for detecting side-scattered light and fluorescence from the fine cell particles by the incident laser beams.

FIG. 6A is an enlarged cross sectional view of the flow cell illustrating a plurality of the second optical detectors opposing to each of the light receiving regions of the flow cell, and FIG. 6B is an enlarged cross sectional view of the flow cell illustrating a plurality of the second optical detectors arranged in an array along vertical and horizontal directions.

FIG. 9 is an enlarged view similar to FIG. 2, showing the optical mechanism of the second embodiment.

FIG. 10A is an enlarged cross sectional view of the flow cell similar to FIG. 5A, and FIG. 10B shows the optical intensity of the incident laser beam which is uniform across each of the light receiving regions of the flow cell, similar to FIG. 5B.

FIG. 12A-12C shows irradiation regions of near ultraviolet laser beams irradiated by the second optical sources according to Comparisons 1-3.

BEST MODE FOR CARRYING OUT THE INVENTION

Figure 1:
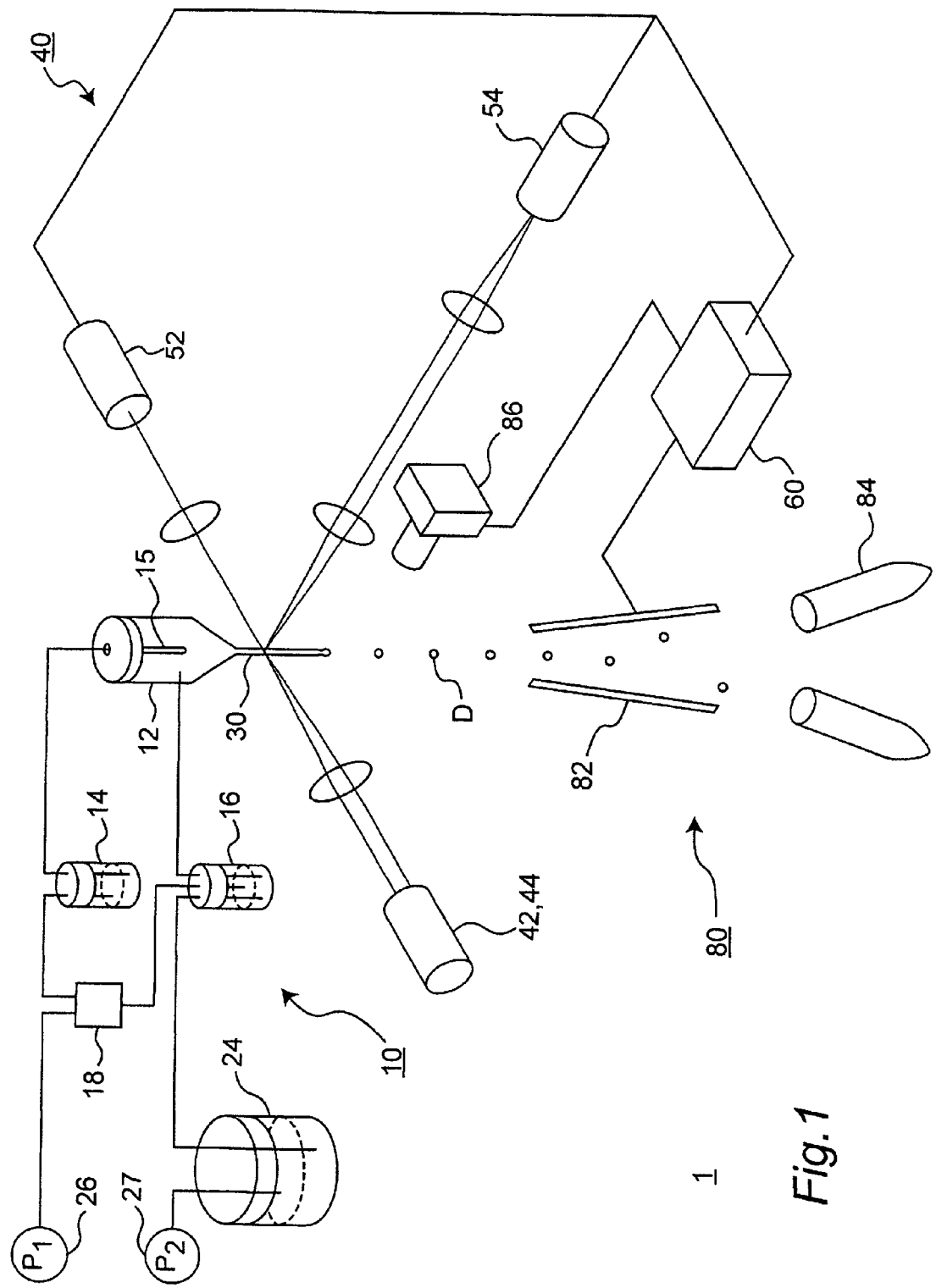
FIG. 1 is a schematic overall view of a flow cytometer (cell sorter) showing a general structure thereof.

Referring to attached drawings, embodiments of a flow cytometer and a cell sorter according to the present invention will be described herein. In the description, a couple of terms for indicating the directions (for example, "upper", "lower", "upstream" or "downstream") are conveniently used just for facilitating clear understandings, it should not be interpreted that those terms limit the scope of the present invention.

Embodiment 1

With reference to FIGS. 1-8, the first embodiment of the flow cytometer and the cell sorter will be described herein. The flow cytometer 1 illustrated in FIG. 1, in general, includes a fluid flow mechanism 10, an optical mechanism 40, and a digital signal processing apparatus (signal processor) 60. The fluid flow mechanism 10 is adapted to define a stream of fine cell particles P (e.g., protein complexes) dyed with a fluorescent labeling reagent, in line within a flow cell 30. The cell particle P may have diameter of a hundred nanometers or less, which is relatively smaller than a typical cell particle such as corpuscles. The optical mechanism 40 is adapted to emit at least two laser beams of different wavelengths onto each of the fine cell particles P and detect various fluorescence and scattering light therefrom. The digital signal processing apparatus 60 is adapted to analyze fluorescence and scattering light by processing electrical signals output from the optical mechanism 40, thereby identifying the fine cell particles P. Also, the flow cytometer 1 may be configured as a cell sorter by incorporating a sorting mechanism 80 for sorting the fine cell particles P by applying to the fine cell particles P, at a given timing, with an electric charge of a polarity varied based upon identification data thereof. More detailed description will be made herein for the fluid flow mechanism 10, the optical mechanism 40, the digital signal processing apparatus 60, and the sorting mechanism 80.

[1. Fluid Flow Mechanism]

Figure 2:
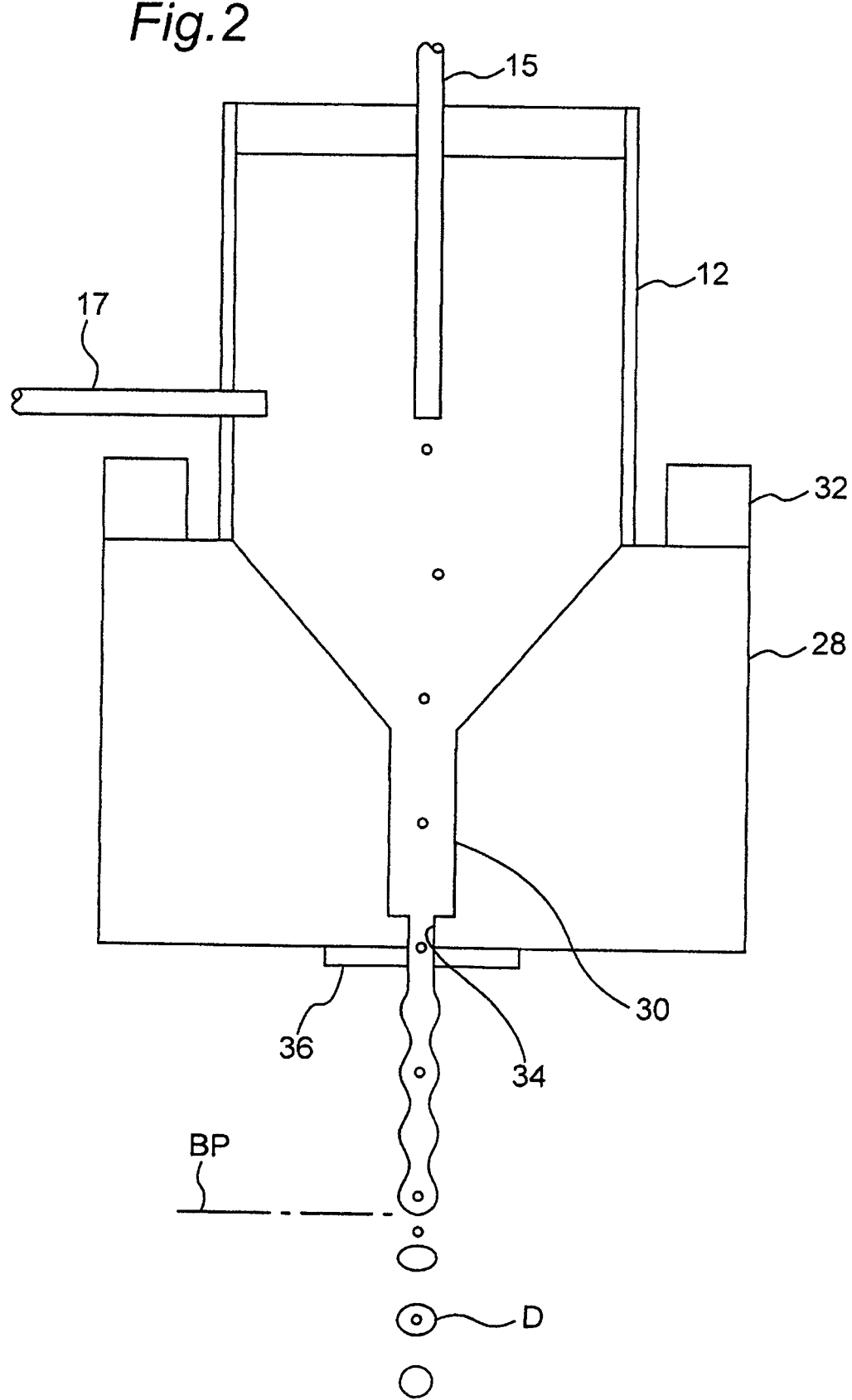
FIG. 2 is an enlarged view of the flow chamber, the flow cell, and the jet flow of the fluid flow mechanism.

With reference to FIGS. 1 and 2, the fluid flow mechanism 10 includes a cylindrical flow chamber 12 for defining a sheath flow, a sample container 14 for receiving sample suspension liquid containing cell particles fluorescently labeled with fluorescent reagents such as fluorescent pigment and a fluorescent-labeled monoclonal antibody, and a sheath container 16 for receiving a sheath liquid. The sample suspension liquid is supplied to a flow chamber 12 from a sample tube 15 aligned along the central axis of the flow chamber 12, while the sheath liquid is supplied to the flow chamber 12 through a sheath tube 17 connected to a peripheral port thereof.

Further, the fluid flow mechanism 10 includes a pressure controller 18 for controlling atmospheric pressure within the sample container 14, an air pump 26 for supplying compressed air to the pressure controller 18, a plenum container 24 for storing a volume of the sheath liquid and supplying it to the sheath container 16, and another air pump 27 for supplying compressed air to the plenum container 24. Preferably, the pressure controller 18 may monitor the pressure within the sheath container 16 and controls it so that pressure within the sample container 14 is greater than that within the sheath container 16, by a predetermined pressure gap.

Also, as illustrated especially in FIG. 2, provided beneath the flow chamber 12 is a funnel-shaped flow-path block 28 made of transparent material such as quartz, glass, fused silica, transparent plastic or the like, downwardly defining a flow path or a flow cell 30 having a horizontal small cross section. Provided on the flow-path block 28 at the peripheral is an oscillator 32 having a piezo-actuator (PZT) oscillating at variable frequency (e.g., f=60 kHz). Further, the flow-path block 28 is provided with an orifice 34 on the bottom and a charging electrode (electric charger) 36 contacting with the sheath flow, for applying electrical charge of desired polarity to a droplet D (containing a fine cell particle P) that is separated from the sheath flow.

In the fluid flow mechanism 10 so structured, upon activation of the air pumps 26, 27, the sample suspension liquid and the sheath liquid are delivered to the flow chamber 12 from the sample container 14 and the sheath container 16, respectively, to form the sheath flow as a cylindrical laminar flow encompassing the sample suspension liquid. Also, upon activation of the oscillator 32, oscillation at a given frequency is applied to the flow-path block 28, so that the sheath flow running through the flow cell 30 is ejected as a jet flow from the orifice 34 of the flow-path block 28, and the horizontal cross section of the jet flow is modulated or constricted along the vertical direction in synchronization with the frequency of the oscillator 32, thereby separating or splitting the droplet D from the jet flow at the break-off point, as shown in FIG. 2.

As will be described later in detail, each of the droplets D containing a fine cell particle P can be charged by applying through the charging electrode 36, a voltage of polarity selected in accordance with identification information of the labeled fine cell particle P, at the timing just before the cell particle P reaches the break-off point. The sorting mechanism 80 includes, as one of its components, a pair of deflectors 82 provided beneath the charging electrode 36, between which a predetermined voltage is applied, so that the charged droplet D is sorted to collection tubes 84, in accordance with the identification information of the fine cell particles P (of electric polarity of the charged droplet D) to be sorted, when dropping between the pair of deflectors 82. Any approaches may be used to obtain identification information of the fine cell particles P may be used, for example, as suggested in above-mentioned Patent Document 2.

[2. Optical Mechanism]

Referring to FIG. 1, the optical mechanism 40 includes first and second optical sources 42, 44 for sequentially emitting laser beams onto each of the fine cell particles P moving in line through the flow cell 30. It also includes a side-scattered light detecting device (first optical detector) 52 for detecting the side-scattered light scattered at the fine cell particle P by the laser beam from the first optical source 41, and a plurality (three, in FIG. 4) of fluorescence detecting devices (second optical detectors) 54, for detecting fluorescence excited by the laser beam from the second optical source 44. In FIG. 4, while the first and second optical sources 42, 44 seem to be opposed to and aligned with the first and second optical detectors 52, 54, respectively, the optical mechanism 40 is actually structured so that the optical axis of the incident laser beams from the first and second optical sources 42, 44 are inclined to those of outputting laser beams to the first and second optical detectors 52, 54, by a certain degree (rather than 180 degrees, preferably 90 degrees). This prevents the first and second optical detectors 52, 54 from detecting the incident laser beams directly from the first and second optical sources 42, 44, and allows precisely detecting the side-scattered light and the fluorescence which have relatively less optical intensity than the incident laser beams.

FIG. 3 is a schematic view showing concrete structure of the optical mechanism 40. In FIG. 3, the first and second optical sources 42, 44 are coherent, emitting light such as coherent laser beams. For example, the first optical source 42 may be a DPSS laser (Diode Pumped Solid State Laser) emitting blue laser beam (peak wavelength: 488 nm, output: 20 mW). The second optical source 44 may be a mode-locked laser emitting near ultra-violet laser beam (peak wavelength: 355 nm, output: 1 W).

In FIG. 3, the blue laser beam from the first optical source 42 is shaped by a beam expander 43a and irradiated onto the upper portion (upstream portion) of the flow cell 30. Also, the near ultra-violet laser beam from the second optical source 44, which typically has Gaussian intensity distribution, is shaped to have substantially even or uniform intensity, by cutting out a portion close to peak of the Gaussian intensity distribution and expanding the cut portion, through an optical attenuator 46, a beam expander 43b, a cylindrical lens 47, a mask 48, and a couple of spherical lens 49a-49c. Thus, the shaped beam with such substantially flat intensity may figuratively be referred to as "derby-hat shaped" beam hereinafter. As a person skilled in the art would easily conceive, any other optical components may be used for shaping the beam to have substantially flat intensity. For example, a beam homogenizer and a diffractive device such as diffractive microscopic lens array, a diffractive beam shaping element, and a diffractive linear focusing lens may be used for converting uneven laser beam to laser beam with uniform intensity.

Figure 5A:
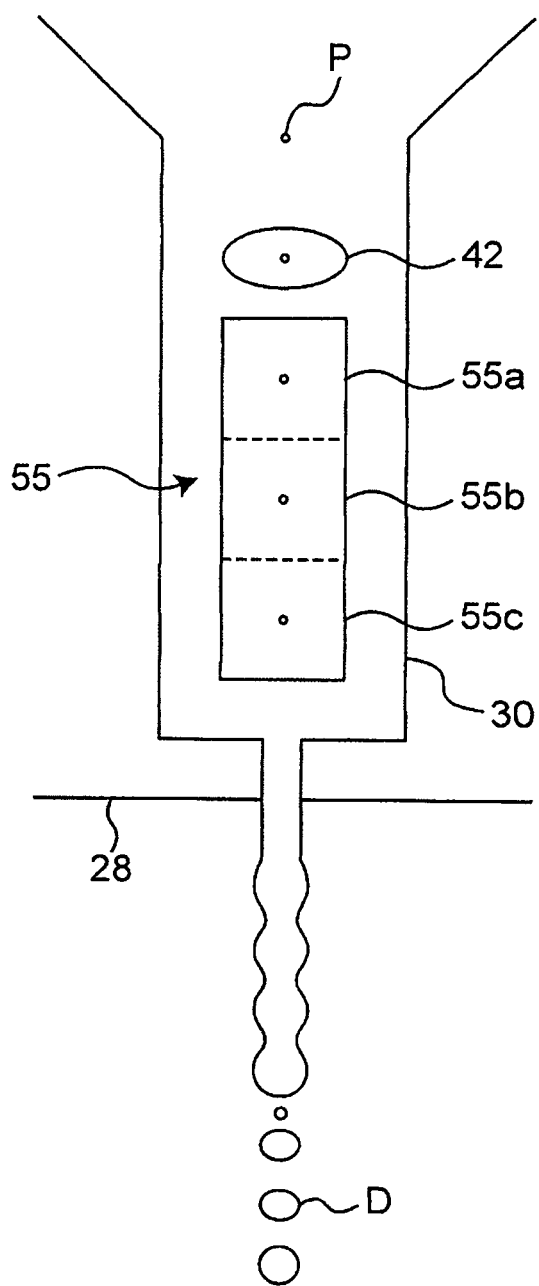
FIG. 5A is an enlarged cross sectional view of the flow cell taken along a plane perpendicular to the irradiation direction of the incident laser beam.

FIG. 4 is an enlarged cross sectional view of the flow cell 30, taken along a vertical plane parallel to the laser beams from the first and second optical sources 42, 44, and also FIG. 5A is an enlarged cross sectional view of the flow cell 30, taken along a vertical plane perpendicular to the laser beams. While the blue laser beam from the first optical source 42 has Gaussian intensity distribution with a peak at the center thereof (not shown), as described above and illustrated in FIG. 5B, the near ultra-violet laser beam from the second optical source 44 is "derby-hat shaped" in a two-dimensional area, i.e., to have substantially uniform intensity across rectangular receiving regions 55a-55c.

The first optical detector 52 may include a typical photodiode to detect only the blue SSC light scattered at the fine cell particles P through a bandpass filter allowing selective passage of the blue laser beam. Each of the second optical detectors 54a-54c is positioned downstream the first optical detector 52 (downward the flow cell 30) opposing to each of the light receiving regions 55a-55c. Each of the second optical detectors 54a-54c may include a photomultiplier or a photon counter (for example, a photon counter, model No. H7421-50, available from Hamamatsu Photonics Kabushiki Kaisha, Hamamatsu, Shizuoka, Japan), detecting red fluorescence from the fine cell particles P excited by the near ultra-violet laser beam, through a bandpass filter (not shown) allowing selective passage of the red light (having wavelength of 610 nm or greater). Thus, each of the second optical detectors 54a-54c detects red fluorescence from the fine cell particles P excited by the laser beam having the same wavelength.

According to one aspect of the present invention, more discussions will be made regarding why the near ultra-violet laser beam from the second optical source 44 is "derby-hat shaped". The fluorescent pigment fluorescently-labeling the fine cell particles P, in general, emits light having energy corresponding to energy gap (band gap) between the ground state and the excited state of electron excited by the excitation beam having energy level higher than the ground state. Also, it is well known that the fluorescence intensity (I) is expressed with parameters, including exciting energy (P) of exciting beam, excitation time period ($\tau_1$), cross sectional area (S) of exciting beam, fluorescence lifetime ($\tau_0$), refraction index (n) of sheath flow, system efficiency factor ($\eta$), in a following equation:

$$I = \eta \times \frac{\tau_1}{\tau_0} \times \left(2 + \frac{Sc/n}{B\tau_0 P}\right)^{-1} \quad (1)$$

wherein "c" represents light speed in vacuum, and "B" represents Einstein's stimulated emission coefficient.

As understood from the above formula (1), while the fluorescence intensity (I) also grows to some extent at beginning as the exciting energy (P) of exciting beam increases, but does not increase much (saturated or unchanged) with greater exciting energy (P), the fluorescence intensity (I) is linearly proportional to excitation time period ($\tau_1$). Thus, in order to increase the fluorescence intensity (I) from few of the fluorescent pigment attached on the fine cell particles P such as the protein complex, it is effective to increase excitation time period ($\tau_1$), that is, time period when the fine cell particles P is excited by the excitation beam.

Thus, according to one aspect of the present invention, the near ultra-violet laser beam from the second optical source 44 is "derby-hat shaped" so that the fine cell particles P are excited effectively by the near ultra-violet laser beam having relatively constant intensity and continuously while passing through the wide receiving regions 55a-55c of the flow cell 30, thereby increasing excitation time period ($\tau_1$) for the greater fluorescence intensity (I).

FIG. 6A illustrates the second optical detectors 54a-54c arranged in line along the passing direction of the sheath flow within the flow cell 30, that is, each of the second optical detectors opposing to the respective one of the light receiving regions 55a-55c of the flow cell 30. Yet, the fine cell particles P may not necessarily pass along the center axis of the flow cell 30, rather possibly run in an off-axis way (i.e., deviating from the center axis) within the flow cell 30. Therefore, in order to receive more fluorescence from the fine cell particles P deviating from the center axis across wider receiving regions 55a-55c, the optical mechanism 40 preferably includes two or more photon counters 54a-54c (three photon counters shown in FIG. 6B) arranged in a horizontal direction perpendicular to the passing direction of the sheath flow. As above, arrangement of the photon counters 54a-54c in a grid array allows more fluorescence from the fine cell particles P to be detected while running through receiving regions 55a-55c of the flow cell 30. Also as shown in FIG. 6B, a plurality of the first optical detectors 52 may horizontally be arranged as well as the second optical detectors 54a-54c.

In other words, since the excitation beam excites the fluorescent dye on the fine cell particles P to release the fluorescence to any directions, it is difficult for a single detector of the conventional flow cytometer to cover all of the fluorescence from the fine cell particles P. However, according to aspects of the present invention, a plurality of the second optical detectors 54 are arranged at least along the vertical running direction of the fine cell particles P within the flow cell 30 so as to collect and detect more fluorescence from the fine cell particles P. Also, according to one aspect of the present invention, a plurality of the second optical detectors 54 are arranged also along the horizontal direction perpendicular to the running direction of the fine cell particles P so as to collect and detect as much as possible of fluorescence released to any directions, thereby improve detecting accuracy of the fine cell particles P.

[3. Digital Signal Processing Apparatus]

As illustrated in FIG. 1, the digital signal processing apparatus (signal processor) 60 is electrically connected both to the side-scattered light detecting device (first optical detector) 52 for detecting the side scattered light when the fine cell particle P is irradiated by the blue laser beam, and a plurality of fluorescence detecting devices (second optical detectors) 54, for detecting red fluorescence excited by the near ultra-violet "derby-hat shaped" laser beam.

Figure 7A:
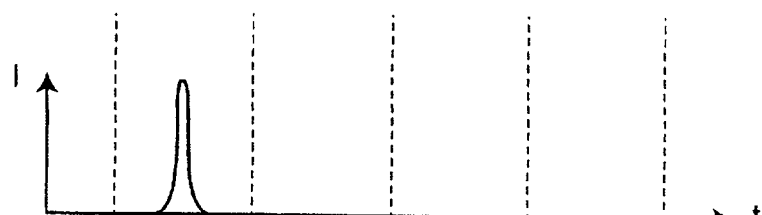
FIG. 7A is a timing chart of electrical signal output from the first optical detector.
Figure 7B:
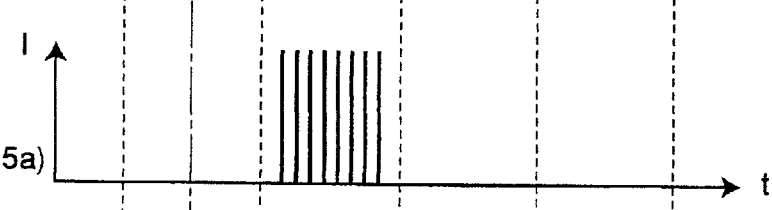
FIGS. 7B-7D are timing charts of electrical signals output from a plurality of the first optical detectors.
Figure 7C:
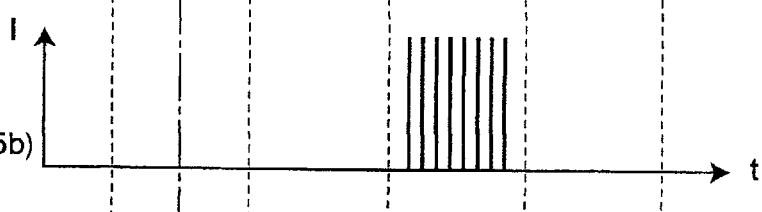
Figure 7D:
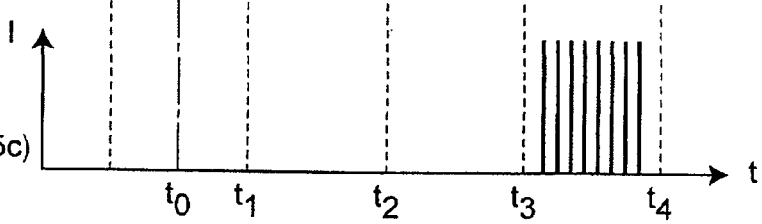

FIG. 7A is a timing chart showing an electric signal output from the photodiode of the first optical detector 52, and also FIGS. 7B-7D each are timing charts showing electric signals output from the photon counters of the second optical detectors 54a-54c, respectively. In general, since the fine cell particle P runs downwardly at a given speed, upon detecting the timing when the electric signal output from the photodiode of the first optical detector 52 has peak intensity (FIG. 7A), the signal processor 60 can estimate time windows (time periods), based upon the timing of the peak intensity, when the fine cell particle P is passing through the receiving regions 55a-55c opposing to the photon counters of the second optical detectors 54a-54c, respectively. Thus, the signal processor 60 can determine the time $t_1$-$t_4$ from the starting point $t_0$, defining the time periods when the fine cell particle P passes through the receiving regions 55a-55c (FIGS. 7B-7D).

The signal processor 60 is adapted to temporarily store electric signals in a buffer memory (not shown) which are detected by the photon counters of second optical detectors 54a-54c during the time windows $t_1$-$t_2$, $t_2$-$t_3$, $t_3$-$t_4$, and to electrically sum those electric signals, so as to amplify the electric signal of the red fluorescence from the targeted fine cell particle P, thereby improving the detecting accuracy Although, in the foregoing description, the optical mechanism 40 are described to have three of the second optical detectors 54a-54c, this is not limited thereto, ten (10) of the photon counters 54 may be arranged along the vertical direction of the sheath flow (flow cell 30), with each center being spaced by 0.25 millimeters from the adjacent one.

A plurality of the fine cell particles P sequentially pass through the flow cell 30, and thus, a particular fine cell particle $P_1$ is followed by the next fine cell particle $P_2$ within the flow cell 30. Nevertheless, the signal processor 60 according to the present invention determines the time windows for each of the fine cell particle $P_1$, $P_2$ and electrically processes those signals regardless the physical positions thereof, and therefore, secures high detection accuracy without interference (crosstalk) of the fluorescence signals to each other.

Further, although not shown in detail, a plurality of microscopic lens may preferably be provided between each of the receiving region 55a-55c and the respective one of the second optical detectors 54a-54c so that the fluorescence from the fine cell particle P can be detected by the second optical detectors 54a-54c more precisely and selectively when the fine cell particle P is running through each of the receiving region 55a-55c. As above, the "derby-hat shaped" excitation intensity of the laser beam from the second optical source 44 allows the fluorescence to be continuously excited and selectively detected by those second optical detectors 54a-54c.

Also, although in the above description, the blue laser beam from the first optical source 42 has Gaussian intensity distribution having peak at the irradiation center; the blue laser beam may also be "derby-hat shaped" to have uniform intensity as well as the near ultra-violet laser beam from the second optical source 44, for irradiation onto the flow cell 30. In this case, a plurality of the first optical detectors 52 may be provided for detecting the blue laser beam for the first optical source 42, so that the time the time $t_1$, $t_2$, $t_3$, $t_4$, defining the time windows when the fine cell particle P passes can be determined in a more precise manner.

In addition, a third optical source or more optical source (not shown) may be provided for irradiating another laser beam having wavelength different from the second laser beam 44, and another optical detector also may be provided to detect fluorescence having different wavelength from the fine cell particles P, thereby collecting more information for identification thereof.

[4. Sorting Mechanism]

Figure 8:
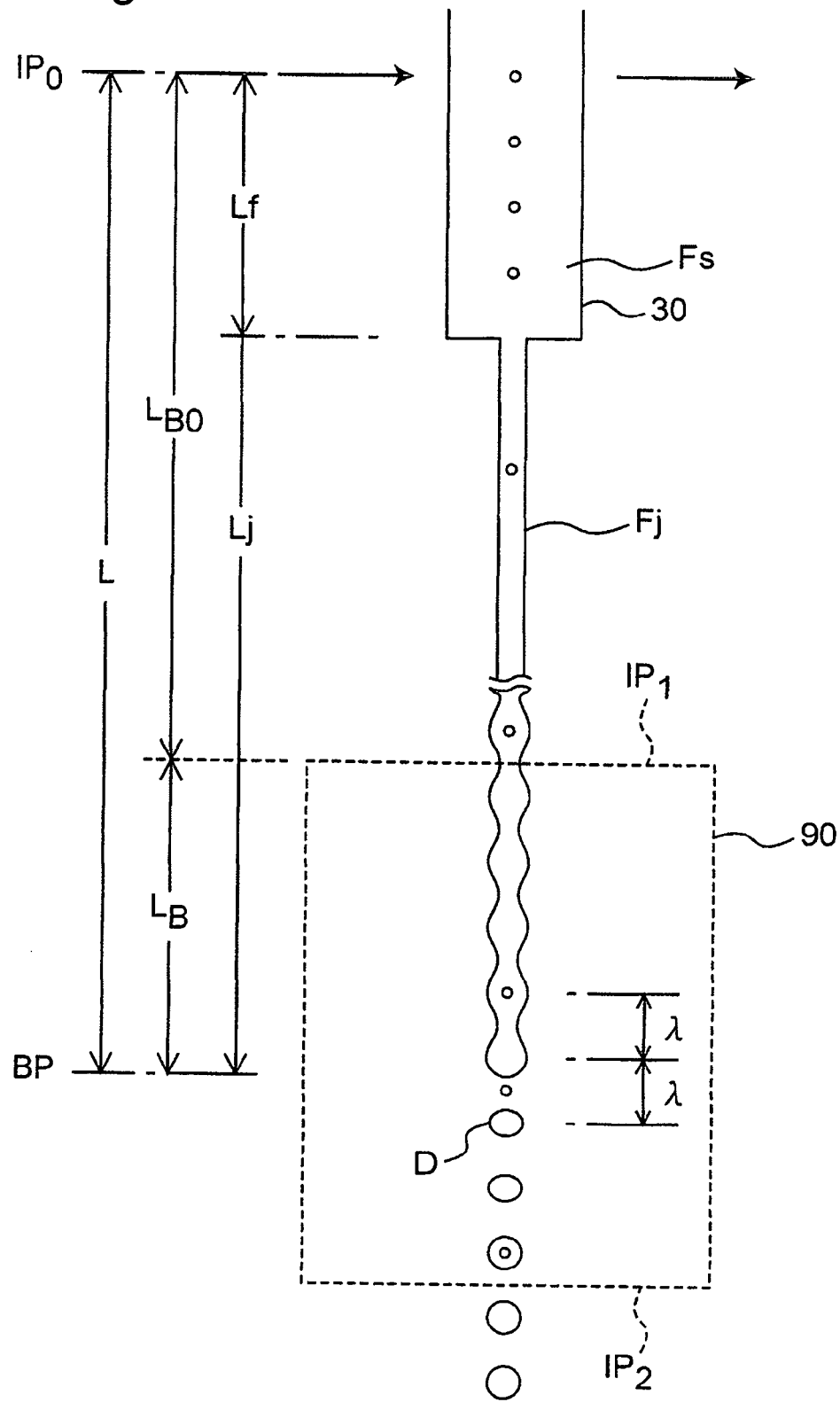
FIG. 8 is a schematic view of the sheath flow within the flow cell and the jet flow (and the droplet split from the jet flow at the break-off point).
Figure 11A:
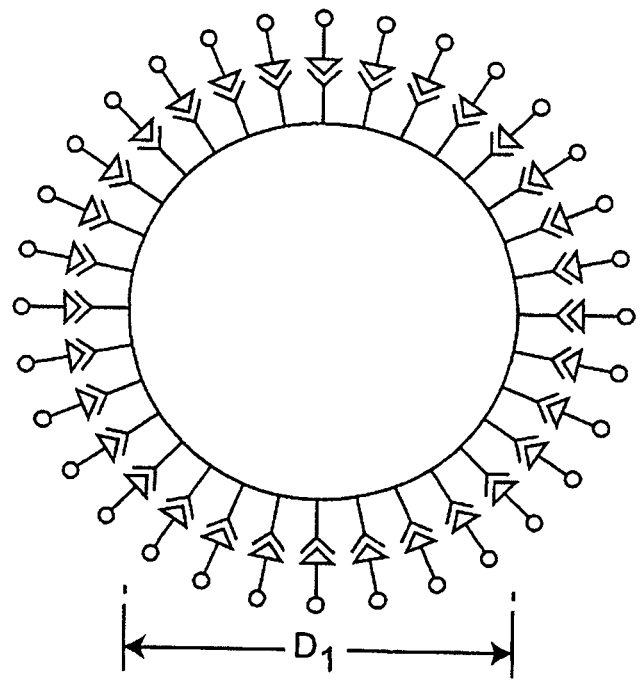
FIG. 11A shows a relatively large cell particle on which a lot of antibodies labeled with fluorescent dye are attached.
Figure 11B:
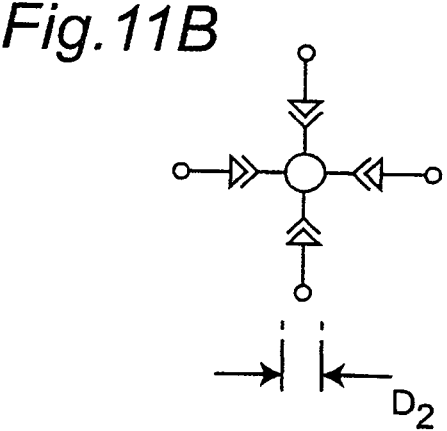
FIG. 11B shows a fine protein complex catching few antibodies labeled with fluorescent dye.

As mentioned above, the cytometer 1 of one aspect according to the present invention may be configured as a cell sorter by incorporating the sorting mechanism 80. With reference to FIGS. 7 and 8, more detailed description will be made herein for the sorting mechanism 80.

The sorting mechanism 80 includes, in general, a pair of deflectors 82, a stationary imaging device 86 having a CCD camera, and a control circuitry (not shown) electrically connected to the imaging device which may be built in the digital signal processing apparatus 60. Thus, although not shown in detail, the digital signal processing apparatus 60 may be connected not only to the deflectors 82 and the stationary imaging device 86, but also to the first and second optical detectors 52, 54, the charging electrode 36 for charging the droplet D, and the oscillator 32 for separating or splitting the droplet D from the jet flow.

FIG. 8 is a schematic view showing the sheath flow $F_S$ in the flow cell 30, the jet flow $F_J$ ejecting from the orifice of the flow cell 30, and a series of the droplets D separated at the break-off point BP from the jet flow $F_J$. As briefly discussed above, when the flow-path block 28 is oscillated by the oscillator 32 provided thereon at a predetermined frequency (for example, f=60 kHz), a horizontal cross section of the jet flow $F_J$ is modulated (varied) along the vertical direction in synchronization with the predetermined frequency of the oscillator 32 as shown in FIG. 8. It should be noted that the modulation period ($\lambda$), i.e., the distance between the adjacent local maximum points or local minimum points, is kept the same as the gap between the adjacent droplets D.

The stationary imaging device 86 having a stroboscopic lamp (not shown) is fixedly arranged at a stationary position relative to the flow cell 30 and designed to take an image of the jet flow $F_J$ and the droplets D close to the break-off point BP in a fixed imaging range defined by a dotted rectangle of FIG. 8, which is partially defined between the imaging upstream and downstream positions $IP_1$, $IP_2$. Also, the stroboscopic lamp is designed to intermittently flicker onto the jet flow $F_J$ and the droplets D in the imaging range at the same frequency (f) as the oscillator 32. Thus, the stationary imaging device 64 takes the image of the jet flow $F_J$ and the droplets D at the same frequency (f), which seems like motionless as illustrated in FIG. 8.

Since the stationary imaging device 86 is fixedly positioned relative to the flow cell 30, the distance ($L_{B0}$) between the position $IP_0$ where the first light detector 52 receives the blue side-scattered light scattered at the fine cell particle P and the imaging position $IP_1$ of the fixed imaging range 70 can be kept constant. Also, the stationary imaging device 64 is used for continuously monitoring the modulation period ($\lambda$) of the jet flow $F_J$, and also the control circuitry is used for calculating the accurate distance L ($L=L_{B0}+L_B$) between the position $P_0$ and the break-off point BP, in real time, by determining the distance ($L_B$) with an image processing technique. Then the accurate distance L is used for correcting the delay time when the fine cell particle P is to be charged by the charging electrode 36 at the break-off point BP. Eventually, the cell sorter can effectively sort the targeted fine cell particle P into some of collection tubes 84, by applying electrical charge of polarity switched based upon identification information of the targeted fine cell particle P, with the jet flow $F_J$ containing the targeted fine cell particle P at the break-off point after the corrected delay time.

Therefore, even in case where the cell particle P to be sorted is very small or fine, the cell sorter incorporating the flow cytometer 1 according to the present invention can electrically sum the fluorescent signals output from the second optical detectors 54a-54c so as to sort the fine cell particles P in a precise manner based upon increased or sufficient information of the fluorescent signals.

Embodiment 2

Referring to FIGS. 9 and 10, a flow cytometer according to the second embodiment of the present invention will be described herein. The flow cytometer 1 of the second embodiment has components similar to those of the first embodiment except that a plurality of the second optical sources 44 are provided, each for emitting laser beam having uniform intensity at the light receiving region 55. Therefore, no duplicate description will be made for the similar components of the second embodiment, which are denoted with similar reference numerals.

As mentioned above, the optical mechanism 40 of the first embodiment is designed to shape the laser beam from a single (second) light source to the beam having substantially uniform intensity across a strip-like long receiving region 55, which may require many components to be assembled and aligned precisely, possibly raising production cost. Also, according to the first embodiment, the laser beam from the single optical source 44 is expanded across the wide receiving regions 55a-55c which may also cover regions where the second optical detectors 54a-54c do not effectively receive the fluorescence, for example, between the adjacent receiving regions 54a-54c. Therefore, optical energy loss may likely be substantial, and increased output power of the second optical source 44 may be required to achieve sufficient optical intensity in each of the receiving regions 55a-55c. In general, a laser beam source of greater output power costs more expensive and requires complicated control to keep optical intensity constant or even, in comparison with one of less output power. Thus, the second embodiment of the present invention is to provide the optical mechanism 40 which is simpler, less expensive, and easy to control.

Figure 5B:
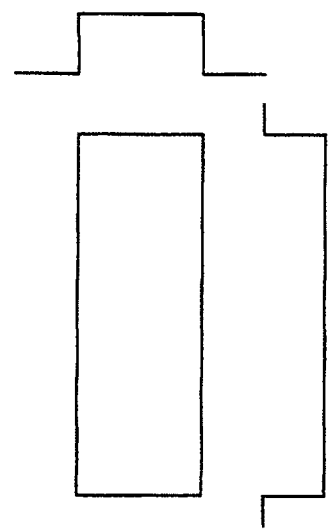
FIG. 5B shows the optical intensity of the incident laser beam which is uniform across the light receiving region of the flow cell.

FIGS. 9, 10A, 10B are enlarged cross sectional views of the flow cell 30, similar to FIGS. 4, 5A, 5B of the first embodiment. In the second embodiment, while the blue laser beam from the first optical source 42 has Gaussian intensity distribution, the near ultra-violet laser beam from each of the second optical source 44 having the identical wavelength is shaped to provides the uniform intensity across the respective one of the rectangular receiving regions 55a-55c of the flow cell 30.

Although the first and second optical sources 42, 44 are illustrated in FIG. 9, to be opposed to and aligned with the first and second optical detectors 52, 54, respectively, as discussed above with reference to FIG. 4, the optical mechanism 40 is actually structured so that the optical axis of the incident laser beams from the first and second optical sources 42, 44 are inclined to those of outputting laser beams to the first and second optical detectors 52, 54, by a certain degree (rather than 180 degrees, preferably 90 degrees). This prevents the first and second optical detectors 52, 54 from detecting the incident laser beams directly from the first and second optical sources 42, 44, and allows precisely detecting the side-scattered light and the fluorescence which have relatively less optical intensity than incident laser beams.

In the flow cytometer 1 structured according to the second embodiment, the signal processor 60 temporarily stores in the buffer memory, the electrical signals detected by the photon counters of the second optical detectors 54a-54c, and electrically sums the signals to amplify (increase) the electrical signal of the red fluorescence from the particular fine cell particle P, for substantial improvement of the detecting accuracy. Also, the cell sorter incorporating the flow cytometer 1 can sort the particular fine cell particles P in a reliable and precise manner.

Further, in order to avoid interference or crosstalk between two fluorescences from a cell particle in one of the light receiving region (e.g., 54b) and another cell particle in the adjacent light receiving region (e.g., 54a, 54c), the optical mechanism 40 according to the second embodiment may be configured to have each of the light receiving regions 55a-55c of the flow cell 30 to be separated or isolated each other. Alternatively the optical mechanism 40 may includes continuous receiving regions 54a-54c and microscopic lens arranged on each of the second optical detectors 54a-54c.

Also, like the first embodiment, the optical mechanism 40 according to the second embodiment may be configured to have a grid array of the second optical detectors (photon counters 54a-54c) arranged in vertical and horizontal directions so as to receive more fluorescent signals (fluorescence intensity) even when the fine cell particle P runs away from the center axis of the flow cell 30.

Further, in order to produce the optical mechanism 40 at more reasonable cost, the near ultra-violet laser beams from the second optical sources 44a-44c may have Gaussian intensity distribution on each of the light receiving regions 55a-55c without being shaped to have uniform intensity, so does the blue laser beam from the first optical source 42. However, even in this case, the near ultra-violet laser beams from the second optical sources 44a-44c should have the identical wavelength.

In another alternative or intermediate embodiment between the first and second embodiments, the optical mechanism 40 may be configured such that the near ultra-violet laser beam output from a single second optical source 44 are shaped into three laser beams divided one another on the rectangular receiving regions 55a-55c.

Example

One example of the flow cytometer 1 according to the present invention will be described herein, which improves detecting or identifying accuracy of desired fine cell particles P in the sample suspension liquid, conferring a comparison of a conventional flow cytometer. In particular, flow cytometers according to Comparison 1 (corresponding to the present invention) and Comparison 2 (corresponding to the conventional flow cytometer) are used to irradiate excitation laser beam onto fluorescently-labeled or targeted standard beads (referred to as "Target Beads") in the sample suspension liquid, thereby to detect the fluorescence intensity from Target Beads excited by the laser beam and to count the numbers thereof. Also, the flow cytometers of Comparisons 1 and 2 are used to irradiate excitation laser beam onto non-fluorescently-labeled or untargeted standard beads (referred to as "Blank Beads") in the same sample suspension liquid, thereby to detect the fluorescence intensity from Blank Beads excited by the laser beam and to count the numbers thereof.

Target Beads used in this example are yellow-fluorescent standard beads (Y170) formed of polyethylene sphere having diameter of 170 micrometers which is fluorescently-labeled with labeling dye of streptavidin (Q-dot 705®), while Blank Beads are the same standard beads without being fluorescently-labeled.

It should be noted that the flow cytometers of Comparisons 1 and 2 used in the example have structures similar to one according to the first embodiment, with exception of the optical mechanism 40 different from the first embodiment as explained below.

The second optical source 44 of the flow cytometer of the above embodiment emits near ultra-violet laser beam (peak wavelength: 355 nm, output: 1 W), which is "derby-hat shaped" to have substantially even or uniform intensity across the light receiving region. The second optical source 44 of the flow cytometer of Comparison 1 (corresponding to the present invention) also emits near ultra-violet laser beam, which has intensity of Gaussian distribution over an oblong receiving region (15 micrometers×30 micrometers) extending along the flow cell 30 (or along the sheath flow) in a vertical direction, as illustrated in FIG. 12A. Meanwhile, the second optical source 44 of the flow cytometer of Comparison 2 (corresponding to the conventional flow cytometer) also emits near ultra-violet laser beam, which has intensity of Gaussian distribution over an oblong receiving region (30 micrometers×15 micrometers) but extending in a horizontal direction, as illustrated in FIG. 12B. Thus, Comparison 1 allows Target Beads and Blank Beads passing along the flow cell 30 through the longer diameter axis (30 micrometers) of the receiving region shown in FIG. 12A, while Comparison 2 merely permits intersecting across the shorter diameter axis (15 micrometers) of the receiving region shown in FIG. 12B. Therefore, Comparison 1 allows longer excitation time that corresponds to $\tau_1$ in the above equation [1] (nearly double) than Comparison 2.

In the flow cytometers of Comparisons 1 and 2, each of the second optical detectors 54a-54c such as photon counters detects yellow fluorescence from the standard beads excited by the near ultra-violet laser beam and outputs to the signal processor 60, an electrical signal equivalent to the numbers of the photons counted in proportional to the intensity of yellow fluorescence. Then, the signal processor 60 processes the signals by electrically summing the signals detected in each of predetermined time windows, in which each of the standard beads passes through the respective receiving region, as illustrated in FIG. 7. As above, since the flow cytometer of Comparison 1 can detect the fluorescence from the standard bead for a longer (nearly double) excitation time $\tau_1$ than that of Comparison 2, the flow cytometer of Comparison 1 may be evaluated as being close to or corresponding to the present invention and the flow cytometer of Comparison 2 may be referred to as being conventional.

In operation, two types of the sample suspension liquids are prepared, one of which contains only Target Beads and the other one of which suspends only Blank Beads. Those sample suspension liquids are filled independently within the sample container 14 of each of the flow cytometers of Comparisons 1 and 2. Like the above embodiment, upon activation of the air pumps 26, 27, the sample suspension liquid and the sheath liquid are delivered to the flow chamber 12 to form the sheath flow as a cylindrical laminar flow. Also, upon activation of the oscillator 32, the flow-path block 28 is oscillated at a given frequency to form the jet flow from the orifice 34 of the flow-path block 28, thereby separating or splitting the droplet D from the jet flow at the break-off point.

For the sample suspension liquid containing only Target Beads, the photon counters of the second optical detectors 54 are used to detect counted photon numbers (corresponding to intensity) of the fluorescence having wavelength unique to the Target Beads. Also, the signal processor 60 is used to measure frequency of each counted photon number (corresponding to event numbers of Target Beads having given intensity being detected) across all of fluorescence received from the sample suspension liquid.

Also for the sample suspension liquid containing only Blank Beads, the second optical detectors 54 are used to detect counted photon numbers (i.e., intensity) of the fluorescence having wavelength same as those detected for the Target Beads, and the signal processor 60 is used to measure frequency of each counted photon number of Blank Beads.

Figure 13:
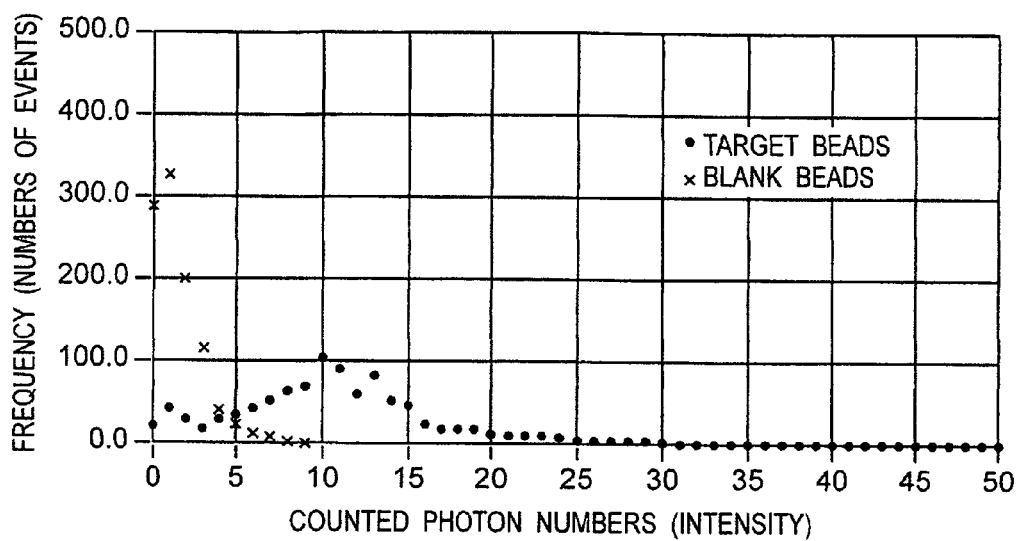
FIG. 13 is a graph illustrating relationships between the counted photon numbers and frequency thereof, for the sample suspension liquids containing Target Beads or Blank Beads, which are detected by the signal processor of Comparison 1.

The signal processor 60 according to the flow cytometer of Comparison 1 (corresponding to the present invention) is used to obtain a graph of FIG. 13, which illustrates relationships between the counted photon numbers of given fluorescence intensities and event frequency of each counted photon number detected from the sample suspension liquids containing either one of Target Beads (as denoted by dots ●) or Blank Beads (as denoted by crosses x). Similarly, the signal processor 60 according to the flow cytometer of Comparison 2 (corresponding to the conventional flow cytometer) is used to obtain a graph of FIG. 14, which shows relationships between the counted photon numbers of fluorescence intensity and event frequency thereof for the sample suspension liquids containing either one of Target Beads (as denoted by dots ●) or Blank Beads (as denoted by crosses x).

Figure 14:
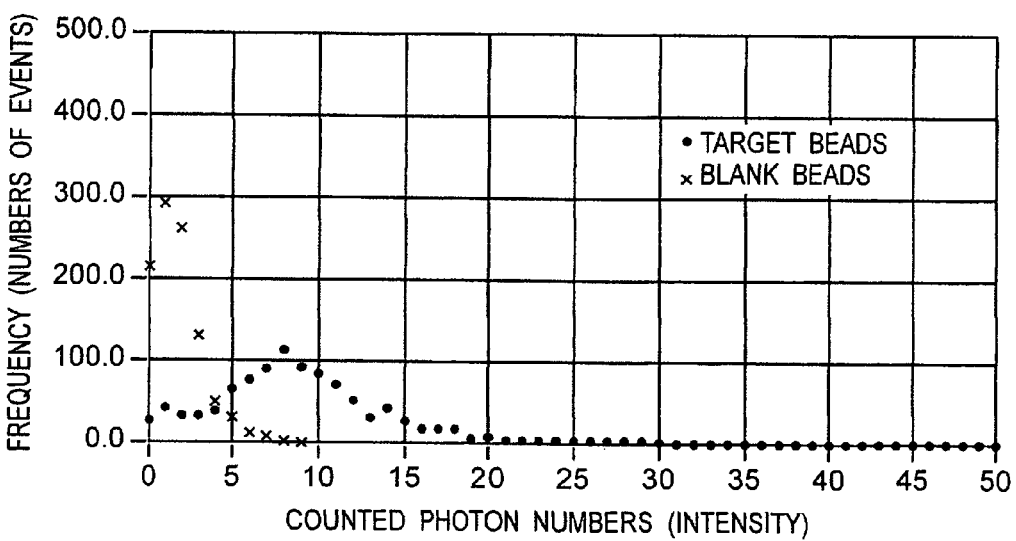
FIG. 14 is a graph illustrating relationships between the counted photon numbers and frequency thereof, for the sample suspension liquids containing Target Beads or Blank Beads, which are detected by the signal processor of Comparison 2.

As clearly shown in those graphs of FIGS. 13 and 14, the counted photon numbers of yellow fluorescence intensity detected from Blank Beads (x) are relatively small or low both in Comparisons 1 and 2. In fact, the averages of the counted photon numbers (average intensity) for all of Blank Beads (x) are 1.45 and 1.72 in Comparisons 1 and 2, respectively, which are almost the same showing no particular superiority. This result can be evaluated as being reasonable and appropriate, since Blank Beads are not fluorescently-labeled standard beads, and the detected fluorescence is due to the background noise.

On the other hand, the averages of the counted photon numbers (average intensity) for all of Target Beads (●) are 11.88 and 9.45 in Comparisons 1 and 2, respectively. Thus, this result shows that Comparison 1 (corresponding to the present invention) increases the average of the counted photon numbers by about 25% or more relative to Comparison 2 (corresponding to the conventional art). Thus, according to the present invention, the average of the counted photon numbers from Target Beads can be increased so as to identify the standard beads in more precise or reliable manner, thereby substantially improving the detecting accuracy thereof.

Figure 15:
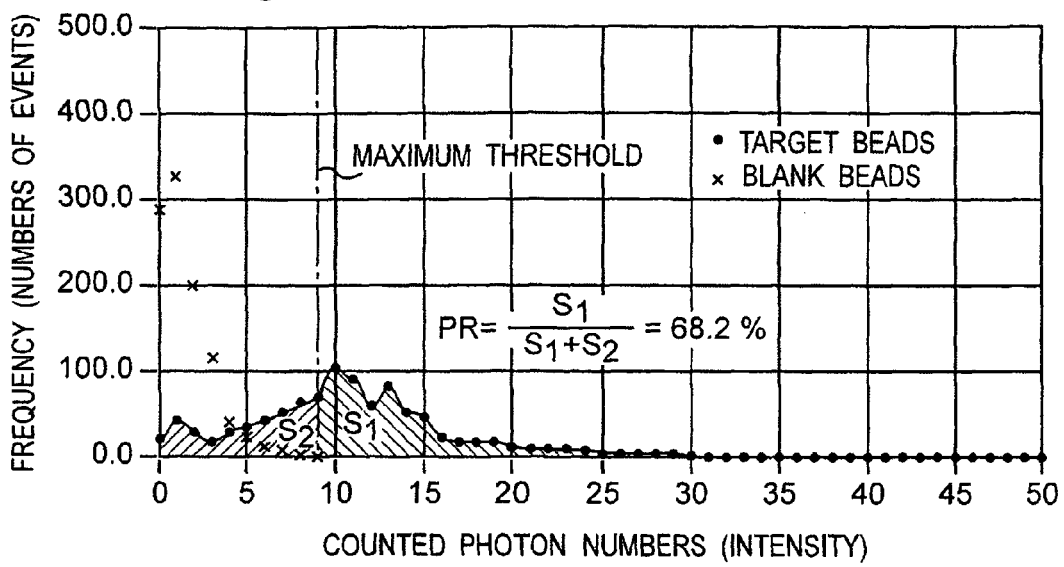
FIG. 15 is a graph similar to FIG. 13, illustrating two areas defined by the counted photon numbers and frequency thereof detected by the signal processor of Comparison 1 for the sample suspension liquids containing Target Beads, which is separated by the maximum threshold of Blank Beads, to obtain the positive ratio.
Figure 16:
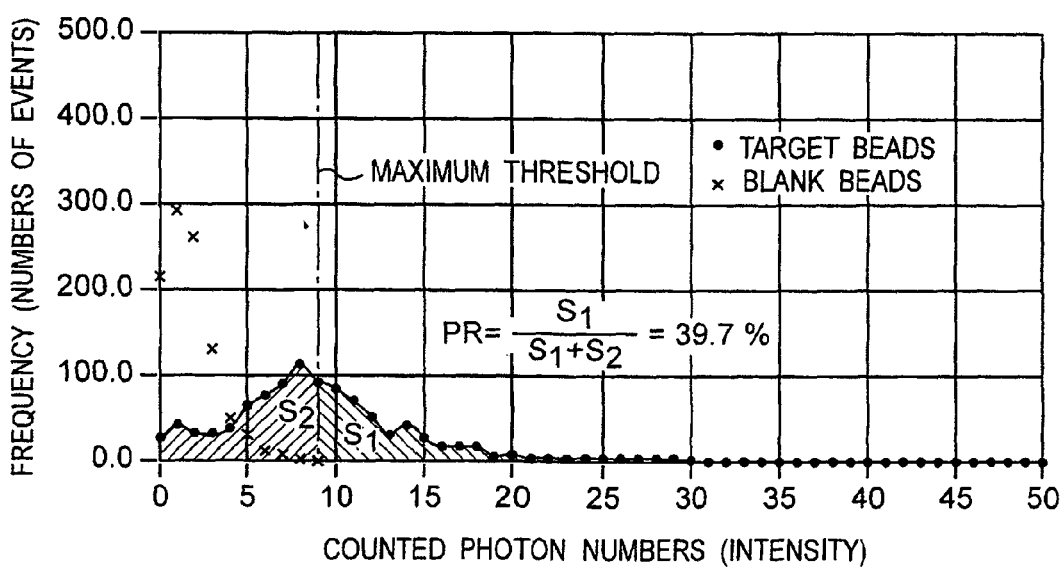
FIG. 16 is a graph similar to FIG. 14, illustrating two areas defined by the counted photon numbers and frequency thereof detected by the signal processor of Comparison 2 for the sample suspension liquids containing Target Beads, which is separated by the maximum threshold of Blank Beads, to obtain the positive ratio.
Figure 17:
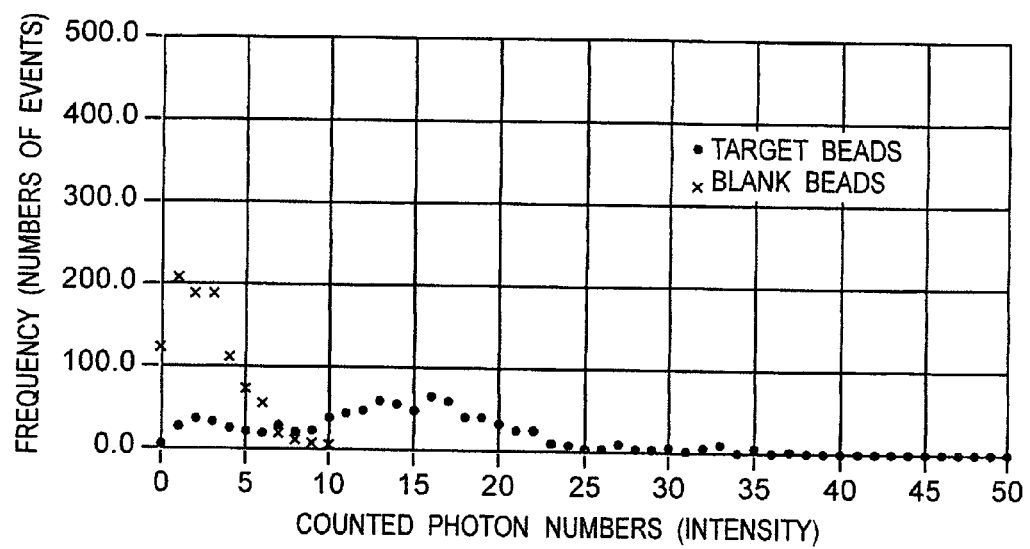
FIG. 17 is a graph illustrating relationships between the counted photon numbers and frequency thereof, for the sample suspension liquids containing Target Beads or Blank Beads, which are detected by the signal processor of Comparison 3.

In order to quantitatively account the detecting accuracy of the standard beads by the flow cytometer, a positive ratio (PR) is defined herein as explained below. As the light intensity due to the background noise is relatively low as mentioned above, a predetermined maximum threshold of the counted photon number (e.g., 9.00) may isolate the Target Beads' fluorescence from the background noise. Further, as illustrated in FIGS. 15 and 16, a series of plotted points for Target Beads (●) are connected via a smooth line, and also first and second areas $S_1$, $S_2$ are defined by this smooth line, the horizontal line of the graph, and the vertical imaginary line indicating the predetermined maximum threshold of the counted photon number. Then the positive ratio (PR) is defined by the following formula.

$$PR(\%)=S_1/(S_1+S_2)$$

Thus, when fluorescence having the counted photon numbers (intensity) greater than the maximum threshold is detected by the signal processor 60, it is securely determined that the fluorescence is due to Target Beads rather than the background noise. Therefore, the sorter mechanism 80 is used with the secure determination of Target Beads, for sorting the Target Beads from Blank Beads in a precise and reliable manner. In other words, yield performance of the fine cell particles P to be sorted by the cell sorter can be increased by improvement of the positive ratio (PR).

In fact, the positive ratios (PR) of Comparisons 1 and 2 are 68.2% and 39.7%, respectively. Therefore, the cell sorter according to Comparison 1 (corresponding to the present invention) achieves the yield performance of the targeted fine cell particles P, which is about 1.7 times greater than that of Comparison 2 (corresponding to the conventional art).

Referring to the flow cytometer of Comparison 3, another approach to further improve the detecting accuracy will be described herein. In the flow cytometer of Comparison 3, while the second optical source 44 has an oblong receiving region similar to one of Comparison 1 as shown in FIG. 12C, the air pumps 26, 27 are controlled to apply less pressure within the sample container 14 and the sheath container 16 so as to reduce the flow rate of the sheath flow (standard beads) within the flow cell 30. For example, while the sheath flow within the flow cell 30 of Comparisons 1, 2 are controlled to have the flow rate of $v_1$ (2.26 m/s), the air pumps 26, 27 are controlled so that the sheath flow within the flow cell 30 of Comparison 3 have the flow rate of $v_2$ (1.55 m/s). Thus, this is a pilot experiment to reduce the flow rate for extending the excitation time. It is confirmed that according to Comparison 3, the averages of the counted photon numbers (average intensity) for Target Beads is increased up to 13.11 so as to secure even more reliable identification of the standard beads (11.88 for Comparison 1), thereby to substantially improve the detecting accuracy.

DENOTATION OF REFERENCE NUMERALS

1 . . . flow cytometer, 10 . . . fluid flow mechanism, 12 . . . flow chamber, 14 . . . sample container, 15 . . . sample tube, 16 . . . sheath container, 18 . . . pressure controller, 24 . . . plenum container, 26,27 . . . air pump, 28 . . . flow-path block, 30 . . . flow cell, 32 . . . oscillator, 34 . . . orifice, 36 . . . charging electrode (electric charger), 40 . . . optical mechanism, 42 . . . first optical source, 43 . . . beam expander, 44 . . . second optical source, 46 . . . optical attenuator, 47 . . . first cylindrical lens, 48 . . . mask, 49 . . . spherical lens, 52 . . . first optical detector, 54 . . . second optical detector, 55 . . . light receiving region, 60 . . . digital signal processing apparatus (signal processor), 80 . . . sorting mechanism, 82 . . . deflectors, 84 . . . collection tube, 86 . . . stationary imaging device, P . . . fine cell particles, D . . . droplet, BP . . . break-off point.

The invention claimed is:

1. A flow cytometer, comprising:
a flow cell configured to define a sheath flow encompassing a dyed biological particle;
a first optical source configured to irradiate a first light onto the dyed biological particle passing through said flow cell;
a second optical source configured to irradiate a second light with non-uniform intensity;
a first optical detector configured to detect scattered light or fluorescence from the biological particle to output a first electrical signal corresponding thereto;
a beam shaper configured to shape the second light to have substantially uniform intensity along a direction of flow of the flow cell, wherein the second light is shaped by said beam shaper to have substantially uniform intensity along the direction of flow of the flow cell and then irradiated onto the dyed biological particle passing through a plurality of light receiving regions in said flow cell downstream from where the first light is irradiated;
a plurality of second optical detectors arranged along said direction of flow of the flow cell, wherein each of said second optical detectors are configured to detect fluorescence from the biological particle in each of the light receiving regions to output a second electrical signal corresponding thereto; and
a signal processor configured to sum the second electrical signals, which are output from the plurality of second optical detectors in a plurality of time windows estimated upon when said first optical detector detects the scattered light or the fluorescence, thereby increasing the second electrical signals of the fluorescence from the biological particle excited by the second light.

2. The flow cytometer according to claim 1, wherein said second optical source includes a plurality of separate optical sub-sources, and wherein each of the optical sub-sources is configured to irradiate the second light having the same wavelength across the plurality of light receiving regions, respectively.

3. The flow cytometer according to claim 1, further comprising a plurality of microscopic lenses opposed to said second optical detectors, respectively, for focusing the fluorescence from the biological particle into said second optical detectors.

4. A cell sorter comprising the flow cytometer according to claim 1 and a sorting mechanism.

5. A flow cytometry method, comprising:
defining a sheath flow encompassing a dyed biological particle;
irradiating a first light onto the dyed biological particle passing through said flow cell;
irradiating a second light with non-uniform intensity;
shaping the second light to have substantially uniform intensity along a direction of flow of the flow cell, wherein the second light is irradiated with substantially uniform intensity onto the dyed biological particle passing through a plurality of light receiving regions in said flow cell downstream from where the first light is irradiated;
detecting scattered light or fluorescence from the biological particle with a first optical detector to output a first electrical signal corresponding thereto;
detecting fluorescence from the biological particle in a plurality of light receiving regions with a plurality of second optical detectors arranged along the direction of flow of the flow cell, to output a second electrical signal corresponding thereto; and
summing the output of second electrical signals in a plurality of time windows estimated upon when said first optical detector detects the scattered light or the fluorescence, thereby increasing the second electrical signals of the fluorescence from the biological particle excited by the second light.

6. The flow cytometry method according to claim 5, wherein the second light is irradiated by a plurality of separate optical sub-sources having the same wavelength across the plurality of light receiving regions, respectively.

7. A flow cytometer, comprising:
a flow cell configured to define a sheath flow encompassing a dyed biological particle, and including a first light receiving region and a plurality of second light receiving regions downstream from the first light receiving region;
a first optical source configured to irradiate a first light onto the first light receiving region of said flow cell;
a second optical source configured to irradiate a second light with non-uniform intensity;
a beam shaper configured to shape the second light to have substantially uniform intensity along a direction of flow of the flow cell, wherein the second light is shaped by said beam shaper to have substantially uniform intensity along the direction of flow of the flow cell and then irradiated onto the plurality of the second light receiving regions of said flow cell;
a first optical detector configured to detect scattered light or fluorescence from the biological particle to output a first electrical signal corresponding thereto;
a plurality of second optical detectors arranged along said direction of flow of the flow cell, wherein each of said second optical detectors are configured to detect fluorescence from the biological particle in the respective second light receiving region to output a second electrical signal corresponding thereto; and
a signal processor configured to sum the second electrical signals, which are output from each of said second optical detectors in a plurality of time windows estimated upon the first electrical signal when the biological particle is passing through each one of the second light receiving regions, thereby increasing the second electrical signal of the fluorescence from the biological particle.

8. The flow cytometer according to claim 7, wherein said second optical source includes a plurality of optical sub-sources, wherein each of the optical sub-sources is configured to irradiate the second light having the same wavelength across the plurality of second light receiving regions, respectively.

9. The flow cytometer according to claim 7, wherein said second optical source includes an array of optical sub-sources arranged in vertical and horizontal directions.

10. The flow cytometer according to claim 7, further comprising a plurality of microscopic lenses positioned between said second optical detectors and the second light receiving regions, for focusing the fluorescence from the cell particle into said second optical detectors.

11. A cell sorter comprising: the flow cytometer according to claim 7 and a sorting mechanism.

12. A flow cytometry method, comprising:
providing a flow cell which defines a sheath flow encompassing a dyed biological particle, and includes a first light receiving region and a plurality of second light receiving regions downstream from the first light receiving region;
irradiating a first light onto the first light receiving region of said flow cell;
irradiating a second light with non-uniform intensity;
shaping the second light to have substantially uniform intensity, wherein the second light is irradiated with substantially uniform intensity along a direction of flow of the flow cell onto the plurality of second light receiving regions of the flow cell;
detecting scattered light or fluorescence from the biological particle to output a first electrical signal corresponding thereto;
detecting fluorescence from the biological particle passing along the direction of flow of the flow cell through each of the second light receiving regions to output a plurality of second electrical signals corresponding thereto; and
summing the second electrical signals in a plurality of time windows estimated upon the first electrical signal, thereby increasing the second electrical signals of the fluorescence from the biological particle.

13. The flow cytometry method according to claim 12, wherein the second light is irradiated by a plurality of individual light sub-sources having the same wavelength.

* * * * *